United States Patent
Papathanassiu

(10) Patent No.: US 9,422,224 B2
(45) Date of Patent: Aug. 23, 2016

(54) METHODS OF TREATMENT USING A BCAT1 INHIBITOR

(75) Inventor: Adonia E. Papathanassiu, Washington, DC (US)

(73) Assignee: ERGON PHARMACEUTICALS LLC, Silver Spring, MD (US)

( * ) Notice: Subject to any disclaimer, the term of this patent is extended or adjusted under 35 U.S.C. 154(b) by 0 days.

(21) Appl. No.: 14/125,687

(22) PCT Filed: Jun. 12, 2012

(86) PCT No.: PCT/US2012/042046
§ 371 (c)(1),
(2), (4) Date: Dec. 12, 2013

(87) PCT Pub. No.: WO2012/173987
PCT Pub. Date: Dec. 20, 2012

(65) Prior Publication Data
US 2014/0128467 A1    May 8, 2014

Related U.S. Application Data

(60) Provisional application No. 61/520,645, filed on Jun. 13, 2011.

(51) Int. Cl.
*A61K 31/19* (2006.01)
*C07C 59/185* (2006.01)

(52) U.S. Cl.
CPC .............. *C07C 59/185* (2013.01); *A61K 31/19* (2013.01)

(58) Field of Classification Search
CPC .............................. C07C 59/185; A61K 31/19
See application file for complete search history.

(56) References Cited

U.S. PATENT DOCUMENTS

2010/0286266 A1    11/2010    Greig
2011/0093962 A1    4/2011    Heidbrink et al.

FOREIGN PATENT DOCUMENTS

WO    2010/127452    11/2010
WO    2012/100957    8/2012

OTHER PUBLICATIONS

PubChem, http://pubchem.ncbi.nlm.nih.gov/compound/796813?from=summary, accessed Dec. 10, 2014.*

(Continued)

*Primary Examiner* — Savitha Rao
*Assistant Examiner* — Angela Brown-Pettigrew
(74) *Attorney, Agent, or Firm* — Wenderoth, Lind & Ponack, L.L.P.

(57) ABSTRACT

The present invention is directed to BCAT inhibitors with the following formula:

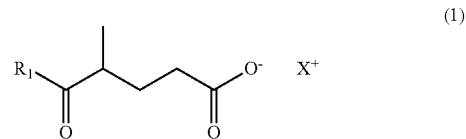

(1)

Wherein $R_1$ is a linear alkyl group and $X^+$ denotes a cation. These inhibitors are useful in treating autoimmune inflammatory diseases such as systemic lupus erythematosus, rheumatoid arthritis, multiple sclerosis, psoriasis and inflammatory bowel disease.

4 Claims, 5 Drawing Sheets

(56) References Cited

OTHER PUBLICATIONS

PubChem (https://pubchem.ncbi.nlm.nih.gov/compound/hexanoic_acid#section=Top, accessed Apr. 18, 2016).*
Holloway, C. et al., Direct Enantioselective Bronsted Acid Catalyzed N-Acyliminium Cyclization Cascades of Tryptamines and Ketoacids, Organic Letters, 2010, 12(21), pp. 4720-4723.
Boers, R. et al., Synthesis and Spectroscopic Characterization of [5-13C]-and [6-13C]-Ubiquinone-10 for Studies of Bacterial Photosynthetic Reaction Centers, European Journal of Organic Chemistry, 2002 (1), pp. 189-202.
International Search Report for PCT/US2012/042046 dated Jan. 29, 2013.
Supplemental European Search Report in European Appln. No. 12 80 0655, dated Oct. 17, 2014.

* cited by examiner

| Immunoblotting | 1 | 2 | 3 | 4 |
|---|---|---|---|---|
| (A) CD147 | | | | |
| (C) Tubulin | | | | |

| Zymographic Analysis | MOHA (mM) | | |
|---|---|---|---|
| | 0 | 10 | 25 |
| MMP2 | | | |
| Ratio | 1.0 | 0.5 | 0.3 |

| Immunoblotting | MOHA | | | | |
|---|---|---|---|---|---|
| MMP9 | - | - | + | + | 200 ng/mL CypA |
|  | - | + | - | + | 10 mM MOHA |
|  | | | | | |
| Protein Ratio | 1.00 | 0.20 | 1.23 | 0.15 | |

METHODS OF TREATMENT USING A BCAT1 INHIBITOR

BACKGROUND ON THE INVENTION

Branched-chain amino acid aminotransferase (BCAT) is the enzyme responsible for catalyzing the first step in the metabolism of branched-chain amino acids (BCAAs) such as leucine, isoleucine, and valine. The step involves the reversible transamination of BCAAs to corresponding branched-chain α-keto acids (BCKAs). BCAT exists in two forms: a cytosolic form (BCAT1) and a mitochondrial form (BCAT2). The two isozymes exhibit distinct and non-overlapping distribution. While BCAT2 is considered ubiquitous, BCAT1 has limited expression and is thought to be found only in embryonic tissues, in adult brain, ovary, and placenta and in c-myc-induced brain tumors and T-cell lymphomas but not in c-myc-induced mammary tumors or B-cell lymphomas (Benvenisty N. et al., An embryonically expressed gene is a target for c-Myc regulation via the c-Myc-binding sequence. *Genes Dev.* (1992) 6:2513-2523).

Expression of the gene which encodes BCAT1 (Bcat1/Eca39) has been associated with proliferation in yeast and increased metastatic potential in human cancers. Schuldiner et al. showed that disruption of the Eca39 homologue in *Saccharomyces cerevisiae* resulted in increased proliferation (Schuldiner O. et al., ECA39, a conserved gene regulated by c-Myc in mice, is involved in G1/S cell cycle regulation in yeast. *Proc. Natl. Acad. Sci. USA* (1996) 93:7743-7748). Eden and Benvenisty suggested that BCAT1 inhibits proliferation through production of α-ketoisocaproate, a leucine metabolite, which was shown to induce apoptotic death (Eden A. and Benvenisty N., Involvement of branched-chain amino acid aminotransferase (Bcat1/Eca39) in apoptosis. *FEBS Let.* (1999) 457:255-261).

Despite the recent advances in designing more effective cancer treatments, cancer remains the second leading cause of death in United States and a major health issue. Metastatic disease, as opposed to primary tumor growth, is usually the cause of cancer mortality. Despite this well-known fact, the majority of new anticancer drugs entering the marketplace focus on reducing tumor burden. It is apparent that what is needed is new drugs that prevent cancer invasion and inhibit cancer metastasis.

Metastatic colonization is governed by the reciprocal interaction of tumor cells with their host microenvironment, which consists of extracellular matrix (ECM) and normal cells such as fibroblasts, endothelial cells, or infiltrating inflammatory cells. The net outcome of this interaction is the production of growth factors, chemokines, and proteases such as vascular endothelial growth factor (VEGF) and extracellular matrix metalloproteinases (MMPs), which collectively facilitate tissue remodeling to allow for metastatic growth. Production of MMPs by tumor and host cells is greatly influenced by CD147, a ubiquitously expressed cell surface glycoprotein. CD147, also known as basigin or extracellular matrix metalloproteinase inducer (EMMPRIN), is grossly upregulated in cancer, where is thought to promote invasion, metastasis, growth, and survival of malignant cells through a multitude of functions. Specifically, cell surface expressed CD147: a) mediates both heterotypic and homotypic cell-cell interactions among tumor cells, fibroblasts, and endothelial cells resulting in synthesis and secretion of MMPs and VEGF, which, in turn, promote tumor angiogenesis, and b) supports anchorage-independent growth of cancer cells and renders tumor cells resistant to anoikis by down-regulating Bim, a pro-apoptotic protein. CD147 is also known to: a) interact with cytoskeletal proteins and participate in the cytoskeleton rearrangement and cell motility, and b) associate with monocarboxylate transporters (MCTs) and facilitate their trafficking to the plasma membrane.

Dysregulation of inflammation, the physiological response to injury, is the hallmark of many autoimmune diseases including but not limited to systemic lupus erythematosus, rheumatoid arthritis (RA), multiple sclerosis (MS), psoriasis, and inflammatory bowel disease. Autoimmune inflammatory diseases are often characterized by elevation of pro-inflammatory cytokines such as tumor necrosis factor-alpha (TNF-α), interleukin-1β (IL-1β), interleukin-6 (IL-6), interleukin-10 (IL-10), and interferon-alpha (IFN-α). The same cytokines may also play a role in the pathogenesis of these diseases (Postal M, Appenzeller S. The role of tumor necrosis factor-alpha (TNF-α) in the pathogenesis of systemic lupus erythematosus. *Cytokine* (2011) 56:537-543).

RA is a chronic, systemic autoimmune inflammatory disease that affects 0.5-1% of the world's adult population, most commonly women between the ages of 30 to 55 years old. It involves the significant alteration of the synovium and leads to musculoskeletal disability and an increased risk of mortality. Synovium is the thin cell layer which envelopes the cavity of synovial joints and produces synovial fluid for joint lubrication. It is composed of two morphologically distinct cell types: the macrophage-like synoviocytes (MLS) and the fibroblast-like synoviocytes (FLS). During RA, CD4$^+$T cells along with macrophages and to a lesser degree B cells, plasma cells, dendritic and mast cells accumulate and invade through the synovial membrane, where they secrete pro-inflammatory signals and assist in the activation of the synovial cells. Secretion of pro-inflammatory cytokines from MLS leads to activation of FLS. Activated FLS aggressively degrade extracellular matrix alone or in co-operation with MLS. Hyperplasia of synoviocytes results in thickening of the synovial lining and its transformation into panus, a tissue mass that invades into articular cartilage and subchondral bone. Invading FLS degrade cartilage through secretion of MMPs and cathepsins. In addition, activated FLS and T cells release receptor activator of NF-κB ligand (RANKL), the protein responsible for the terminal differentiation of precursor myeloid cells into osteoclasts. In advanced RA, increased osteoclastogenesis leads to bone erosion (Pettit A R et al., RANKL protein is expressed at the pannus-bone interface at sites of articular bone erosion in rheumatoid arthritis. *Rheumatology* (Oxford) (2006) 45:1068-1076).

A number of options for the treatment of RA exist including non-steroidal anti-inflammatory drugs (NSAIDS), non-biologic disease-modifying anti-rheumatic drugs (DMARDs), and biologic DMARDs (Quan L D et al., *Expert Opin Ther Pat* (2008) 18(7):723-738). However, each of these options has drawbacks. NSAIDs provide immediate relief from pain and stiffness but are unable to halt the clinical progression of the disease. Biologic DMARDs such as those aiming at inhibiting TNFα are injectable and expensive drugs that exhibit long $t_{1/2}$ and, thus, not easily eliminated in the case of toxicity. Toxic effects associated with the use of DMARDs include life-threatening infections and development of leukemia. It is apparent that what is desired is the development of new anti-rheumatic drugs that can be given orally, are inexpensive, and exhibit short $t_{1/2}$. Since the majority of DMARDs treat RA by reducing inflammation without protecting against bone loss, it is further apparent that what is needed is anti-arthritic agents that can inhibit inflammation while inhibiting bone damage.

Bone homeostasis is maintained by two distinct cell populations: the bone-resorbing osteoclasts and the bone-forming osteoblasts. Normal bone remodeling is influenced by several factors including the RANKL/RANK pathway. RANKL, released by osteoblasts, binds to its cognate receptor RANK present on pre-osteoclastic cells such as monocytes/macrophages and induces their differentiation into mature osteoclasts (Silva I, Branco J C, Rank/Rankl/opg: literature review. *Acta Rheumatol. Port.* (2011) 36(3):209-218). RANKL overproduction leads to an imbalance between the amount of bone removed by osteoclasts and bone formed by osteoblasts and results in decreased skeletal integrity and risk of fracture. Bone diseases mediated by RANKL include but not limited to osteoarthritis, osteoporosis, and periodontal disease, giant cell tumor of the bone, and bone loss associated with chronic obstructive pulmonary disease. These pathological conditions are often associated with elevated levels of circulating RANKL.

SUMMARY OF THE INVENTION

In a first embodiment, the present invention provides methods for the treatment of cancer comprising administering to a subject having cancer a therapeutically effective amount of a BCAT1 inhibitor and a pharmaceutically acceptable carrier. In aspects of this embodiment, the BCAT1 inhibitor is a compound selected from the group of compounds encompassed by formula (1):

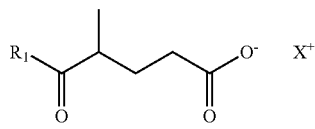

(1)

wherein $R_1$ is hydrogen, a linear or a cyclic alkyl group, an alkylene group, substituted or unsubstituted aromatic ring, an alkoxy, or an alkylamino group and $X^+$ is a cation including but not limited to $Na^+$, $K^+$, and $NH_4^+$.

In aspects of this embodiment, the cancer is characterized by overexpression of CD147, thus, the invention provides methods for treating cancers overexpressing CD147. In this and other aspects, the cancer is selected from the group consisting of breast cancer, prostate cancer, lung cancer, brain cancer, ovarian cancer, colorectal cancer, pancreatic cancer, kidney cancer, skin cancer, liver cancer, head and neck cancer, gastrointestinal cancer, oral carcinomas and leukemias.

In a second embodiment, the invention provides methods for the treatment of an autoimmune inflammatory disease comprising administering to a subject having an autoimmune inflammatory disease a therapeutically effective amount of a BCAT1 inhibitor and a pharmaceutically acceptable carrier. In aspects of this embodiment, the BCAT1 inhibitor is a compound selected from the group of compounds encompassed by formula (1) as set forth above.

In aspects of this embodiment, the autoimmune inflammatory disease is systemic lupus erythematosus, rheumatoid arthritis (RA), multiple sclerosis (MS), psoriasis, or inflammatory bowel disease.

In a third embodiment, the invention provides methods for the treatment of a pathological condition in a subject, comprising administering to a subject having a pathological condition characterized by overexpression of RANKL and bone loss a therapeutically effective amount of a BCAT1 inhibitor and a pharmaceutically acceptable carrier. In aspects of this embodiment, the BCAT1 inhibitor is a compound selected from the group of compounds encompassed by formula (1) as set forth above.

In aspects of this embodiment, the pathological condition is osteoarthritis, osteoporosis, periodontal disease, giant cell tumor of the bone, or bone loss associated with chronic obstructive pulmonary disease.

In preferred aspects of each embodiment, the BCAT1 inhibitor is 4-methyl-5-oxohexanoic acid (MOHA) or a salt thereof. In other preferred aspects of each embodiment, the subject is a human.

DETAILED DESCRIPTION OF THE INVENTION

Figures 1, 2, 3:
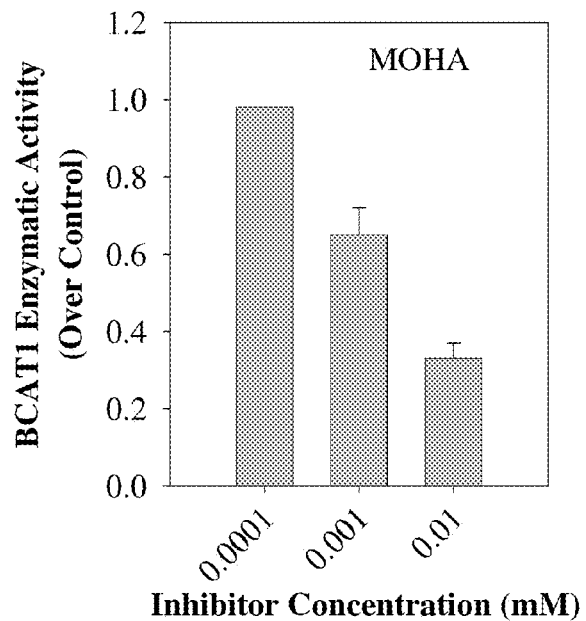
FIG. 1 shows inhibition of BCAT1 by the sodium salt of 4-methyl-5-oxohexanoic acid (MOHA), a formula (1) compound, where $R_1$ is $CH_3$ and X is Na.
FIG. 2 shows down-regulation of the cell surface expression of CD147 after treatment of MDA-MB-231 cells with MOHA. Lane 1: surface biotinylated proteins; cells treated with 0 mM MOHA. Lane 2: surface biotinylated proteins; cells treated with 25 mM MOHA. Lane 3: total proteins; cells treated with 0 mM MOHA. Lane 4: total proteins; cells treated with 25 mM MOHA.
FIG. 3 shows down-regulation of secreted MMP2 from human dermal fibroblasts (HDFs) treated with MOHA.

Other objects, features and aspects of the present invention are disclosed in, or are obvious from, the following Detailed Description. It is to be understood by one of ordinary skill in the art that the present discussion is a description of exemplary embodiments only and is not intended as limiting the broader aspects of the present invention, which broader aspects are embodied in the exemplary construction.

The present invention provides in a first embodiment methods for the treatment of cancer comprising administering to a subject having cancer a therapeutically effective amount of a BCAT1 inhibitor and a pharmaceutically acceptable carrier. In aspects of this embodiment, the BCAT1 inhibitor is a compound selected from the group of compounds encompassed by formula (1):

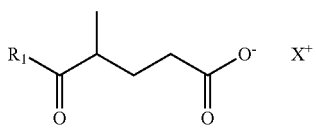

(1)

wherein R₁ is hydrogen, a linear or a cyclic alkyl group, an alkylene group, substituted or unsubstituted aromatic ring, an alkoxy, or an alkylamino group and X⁺ is a cation including but not limited to Na⁺, K⁺, and NH₄⁺. In aspects of this embodiment, the cancer is characterized by overexpression of CD147, thus, the invention provides methods for treating cancers overexpressing CD147. In particular aspects, a cancer characterized by overexpression of CD147 is a cancer selected from the group consisting of breast cancer, prostate cancer, lung cancer, brain cancer, ovarian cancer, colorectal cancer, pancreatic cancer, kidney cancer, skin cancer, liver cancer, head and neck cancer, gastrointestinal cancer, oral carcinomas and leukemias.

The invention provides in a second embodiment methods for the treatment of an autoimmune inflammatory disease comprising administering to a subject having an autoimmune inflammatory disease a therapeutically effective amount of a BCAT1 inhibitor and a pharmaceutically acceptable carrier. In aspects of this embodiment, the BCAT1 inhibitor is a compound selected from the group of compounds encompassed by formula (1) as set forth above. In aspects of this embodiment, the autoimmune inflammatory disease is systemic lupus erythematosus, rheumatoid arthritis (RA), multiple sclerosis (MS), psoriasis, or inflammatory bowel disease.

The invention provides in a third embodiment methods for the treatment of a pathological condition in a subject, comprising administering to a subject having a pathological condition characterized by overexpression of RANKL and bone loss a therapeutically effective amount of a BCAT1 inhibitor and a pharmaceutically acceptable carrier. In aspects of this embodiment, the BCAT1 inhibitor is a compound selected from the group of compounds encompassed by formula (1) as set forth above. In aspects of this embodiment, the pathological condition is osteoarthritis, osteoporosis, periodontal disease, giant cell tumor of the bone, or bone loss associated with chronic obstructive pulmonary disease.

The present invention also includes the use of a BCAT1 inhibitor and a pharmaceutically acceptable carrier in the preparation of a pharmaceutical composition for treating cancer in a subject. The BCAT1 inhibitor is a compound selected from the group of compounds encompassed by formula (1) as set forth herein. The cancer is characterized by overexpression of CD147. In particular aspects, the cancer is a cancer selected from the group consisting of breast cancer, prostate cancer, lung cancer, brain cancer, ovarian cancer, colorectal cancer, pancreatic cancer, kidney cancer, skin cancer, liver cancer, head and neck cancer, gastrointestinal cancer, oral carcinomas and leukemias.

The present invention further includes the use of a BCAT1 inhibitor and a pharmaceutically acceptable carrier in the preparation of a pharmaceutical composition for treating an autoimmune inflammatory disease in a subject. The BCAT1 inhibitor is a compound selected from the group of compounds encompassed by formula (1) as set forth herein. The autoimmune inflammatory disease is systemic lupus erythematosus, rheumatoid arthritis (RA), multiple sclerosis (MS), psoriasis, or inflammatory bowel disease.

The present invention yet further includes the use of a BCAT1 inhibitor and a pharmaceutically acceptable carrier in the preparation of a pharmaceutical composition for treating a pathological condition in a subject, wherein the pathological condition is characterized by overexpression of RANKL and bone loss. The pathological condition is osteoarthritis, osteoporosis, periodontal disease, giant cell tumor of the bone, or bone loss associated with chronic obstructive pulmonary disease.

I. DEFINITIONS

The term "a", "an" and "the" as used herein are defined to mean one or more and includes the plural unless the context is inappropriate.

The term "cancer" relates to any uncontrolled cell growth characterized by overexpression of CD147. Specific examples include but not limited to breast, prostate, lung, brain, ovarian, colorectal, pancreatic, kidney, skin, liver, head and neck, gastrointestinal, oral carcinomas and leukemias.

The term "inhibitor" refers to a substrate that blocks or suppresses the activity of an enzyme and it includes reversible, irreversible, competitive, and noncompetitive inhibitors.

The term "alkyl" means a monovalent hydrocarbon radical.

The term "alkylene" means a divalent hydrocarbon radical.

The term "alkoxy" means a —OR radical, where R is an alkyl as defined above.

The term "alkylamino" means a —NHR radical, where R is an alkyl as defined above.

As used herein, the terms "treat", "treating" and "treatment" have their ordinary and customary meanings, and include one or more of, ameliorating a symptom of a disease, blocking or ameliorating a recurrence of a symptom of a disease, decreasing in severity and/or frequency a symptom of a disease. Treatment means ameliorating, blocking, reducing, decreasing or inhibiting by about 1% to about 100% versus a subject to which the treatment has not been administered. Preferably, the ameliorating, blocking, reducing, decreasing or inhibiting is about 100%, about 99%, about 98%, about 97%, about 96%, about 95%, about 90%, about 80%, about 70%, about 60%, about 50%, about 40%, about 30%, about 20%, about 10%, about 5% or about 1%. The treatment may begin prior to, concurrent with, or after the onset of clinical symptoms of the disease. Thus, the subject may have a disease or merely be susceptible to the disease. The results of the treatment may be permanent or may continue for a period of days (such as 1, 2, 3, 4, 5, 6 or 7 days), weeks (such as 1, 2, 3 or 4 weeks) or months (such as 1, 2, 3, 4, 5, 6 or more months).

The term "subject" is intended to mean an animal, such birds or mammals, including humans and animals of veterinary or agricultural importance, such as dogs, cats, horses, sheep, goats, and cattle.

A kit comprising one or more of the BCAT1 inhibitors of formula (1) of the present invention, along with printed instructions for the use of the inhibitors in the various methods described herein, is also within the purview of the present invention.

II. SUITABLE METHODS FOR PRACTICING THE INVENTION

In Vitro Tumor Cell Proliferation Assay. The ability of a BCAT1 inhibitor to suppress cancer growth is evaluated in vitro using a cell proliferation assay. A cell proliferation assay typically involves the routine culturing of a cell line to near confluency in the appropriate media. Subsequently, the cells are trypsinized and plated on a 96-well plate at 2,000 or 5,000 cell per well. The cells are cultured for 48 to 96 hours in the presence or absence of the inhibitor. Cell proliferation is then determined using spectrophotometry (MTT assay, BrdU assay) or fluorimetry (Cyquant assay).

In Vivo Metastatic Assay.

The ability of a BCAT1 inhibitor to suppress cancer growth is evaluated in vivo using a spontaneous metastatic tumor model. In this model, a certain number of cells from a pro-metastatic cell line (e.g., MDA-MB-231) are injected subcutaneously in athymic nude mice. The tumor cells are allowed to grow and treatment is initiated when the tumors become palpable. When the average tumor volume of control (untreated) mice reaches~1000 mm$^3$, tumors are surgically removed under anesthesia and the wounds are closed. Treatment continues for a few more weeks. At the end of the experiment, the animals are sacrificed and the target organs are removed and examined for the presence of metastases.

Activation of Synovial Cells.

RA pathology is associated with the sustained activation of synovial cells to produce pro-inflammatory proteins. Antirheumatic agents are tested in vitro for their ability to inhibit secretion of pro-inflammatory proteins from macrophages and fibroblasts in the presence of an inflammatory stimulus such as LPS. At the end of the experiment, secretory proteins are detected in the conditioned media of the cells via an immunological assay such as ELISA or Western immunoblotting.

CIA Model.

CIA is a well known animal inflammation model of RA. In this model, joint arthritis is induced in rats or mice through immunization with heterologous type II collagen in adjuvant and clinically manifested by the presence of erythema and edema in the extremities of the animals. Commonly, antirheumatic agents are administered at the onset of arthritis or upon clinical manifestation. During the experiment, the animals are scored for the presence of arthritis.

Administration.

The compositions described previously may be administered by the topical, oral, rectal or parenteral (intravenous, subcutaneous or intramuscular) route. They may also be incorporated into biodegradable polymers for sustained release implanted at the disease site. The dosage of the compositions depends on the condition treated, the activity of the drug used, the route of administration, and other clinical factors such as severity of the disease and weight of the patient. The compositions are formulated in ways suitable for the specific route of administration.

Formulations suitable for oral administration include capsules, cachets or tablets containing a predetermined amount of the active ingredient, powder or granules, solutions, suspensions, and emulsions. Formulations suitable for topical administration in the mouth include lozenges, pastilles, and mouthwashes. Formulations suitable for topical administration to the skin include ointments, creams, gels, pastes, and transdermal patches. Formulations for rectal administration may be presented as a suppository with a suitable base, while vaginal administrations maybe presented as pessaries, tampons, creams, gels, pastes, foams, and sprays comprising the active ingredient in an appropriate carrier. Formulations suitable for parenteral administration include aqueous and non-aqueous sterile injection solutions presented in unit-dose or multi-dose containers. It should be also understood that, in addition to the ingredients mentioned above, formulations of this invention might include other agents conventional in the art having regard to the type of formulation in question.

In each of the embodiments of the invention, the BCAT1 inhibitors may be administered alone or in combination with a pharmaceutically acceptable excipient. Whether administered alone or in combination with an excipient, formulations comprising one or more BCAT1 inhibitors are administered to a subject in an amount which is effective for treating the specific disease or condition. In general, formulations comprising one or more BCAT1 inhibitors are administered to a subject in an amount of from about 0.1 mg/kg to about 10 mg/kg body weight. Acceptable ranges also include: from about 0.1 mg/kg to about 5 mg/kg, 0.1 mg/kg to about 4 mg/kg, 0.1 mg/kg to about 3 mg/kg, 0.1 mg/kg to about 2 mg/kg, 0.5 mg/kg to about 5 mg/kg, 1 mg/kg to about 5 mg/kg, 1.5 mg/kg to about 5 mg/kg and 2 mg/kg to about 5 mg/kg. Specific dosages of BCAT1 inhibitors in formulations include: 0.1 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1 mg/kg, 1.1 mg/kg, 1.2 mg/kg, 1.3 mg/kg, 1.4 mg/kg, 1.5 mg/kg, 1.6 mg/kg, 1.7 mg/kg, 1.8 mg/kg, 1.9 mg/kg, 2 mg/kg, 2.1 mg/kg, 2.2 mg/kg, 2.3 mg/kg, 2.4 mg/kg, 2.5 mg/kg, 2.6 mg/kg, 2.7 mg/kg, 2.8 mg/kg, 2.9 mg/kg, 3 mg/kg, 3.1 mg/kg, 3.2 mg/kg, 3.3 mg/kg, 3.4 mg/kg, 3.5 mg/kg, 3.6 mg/kg, 3.7 mg/kg, 3.8 mg/kg, 3.9 mg/kg, 4 mg/kg, 4.1 mg/kg, 4.2 mg/kg, 4.3 mg/kg, 4.4 mg/kg, 4.5 mg/kg, 4.6 mg/kg, 4.7 mg/kg, 4.8 mg/kg, 4.9 mg/kg, and 5 mg/kg. However, the amount of BCAT1 inhibitor in formulations administered to a subject will vary between wide limits, depending upon the location, source, identity, extent and severity of the disease or condition, the age and condition of the individual to be treated, etc. A physician will ultimately determine appropriate dosages to be used. Administration frequencies of formulations comprising one or more BCAT1 inhibitors will also vary depending on factors that include the disease or condition being treated and the modes of administration. Each formulation may be independently administered 4, 3, 2 times or once daily, every other day, every third day, every fourth day, every fifth day, every sixth day, once weekly, every eight days, every nine days, every ten days, bi-weekly, monthly and bi-monthly.

The invention is further understood by the following non-limiting examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLE 1

Inhibition of BCAT1 Enzymatic Activity by MOHA

The ability of MOHA to inhibit BCAT1 enzymatic activity was confirmed spectrophotometrically. In this experiment, BCAT1 found in 0.1 mg of MDA-MB-231 tumor cells was immunoprecipitated using 0.25 µL of an anti-BCAT1 antibody and 5 µL protein A agarose beads (Invitrogen). The beads were added to 95 µL of a reaction buffer containing 5 µL pyridoxal 5'-phosphate (PLP), 50 mM ammonium sulfate, 0.05 mM NADH, 5 mM DTT, 5 mM a-ketoglutarate, 10 mM leucine, and 0.95 U leucine dehydrogenase (EMD Chemicals) and various concentrations of MOHA. Addition of BCAT1-bound beads to the reaction mixture led to the consumption of NADH, which was measured fluorometrically (ex:330-370 nm; em:450 nm). The rate of change of fluorescence was then estimated over of period of 10 min (10 cycles; 1 cycle/min). The assay was performed in triplicate in a 96-well plate. FIG. 1 shows that MOHA inhibits the enzymatic activity of BCAT1 at concentrations >100 nM.

EXAMPLE 2

Inhibition of Cell Surface Expression of CD147

MDA-MB-231 cells were plated onto 35 mm culture dishes and allowed to grow to ~80% confluency. They were then treated with 25 mM of MOHA for 24 hrs. At the end of the experiment, cells were subjected to surface biotinylation using EZ-Link Sulfo-NHS-Biotin (Pierce, Thermo Scientific) according to manufacturer's instructions. Following cell lysis, biotinylated proteins were immunoprecipitated from equal (~0.4 mg) amounts of cell lysates using Immobilized Neutravidin Biotin Binding Protein (Pierce, Thermo Scientific) and eluted in loading buffer under reducing conditions by heating at 75° C. for 10 min. Eluted biotinylated proteins were subjected to SDS-PAGE electrophoresis and Western immunoblotting against CD147. The experiment also included 0.2 mg of non-biotinylated cell lysates as a means to determine total levels of CD147 present in MOHA treated cancer cells. FIG. 2 shows that treatment of MDA-MB-231 cells with MOHA results in downregulation of the cell surface expression of CD147.

EXAMPLE 3

Inhibition of MMP2 Secretion

Since the majority of MMPs within human tumors are produced by stromal fibroblasts rather than tumor cells, the effect of a BCAT1 inhibitor on MMP production in cancer is better understood using fibroblasts. Confluent HDF monolayers plated on a 96-well plate were treated with 0, 10, or 25 mM MOHA in serum free DMEM containing 2% BSA. Culture supernatants were collected 24 hrs later. After normalization against the number of cells present, conditioned media were subjected to gelatin zymographic analysis under non-reducing conditions. After a brief (30 min) incubation in 2.5% Triton X-100 in 50 mM Tris buffer (pH 7.5) to renature resolved proteins, the gels were incubated in 50 mM Tris (pH 7.5) containing 1% Triton X-100, 5 mM $CaCl_2$, and 10 µM $ZnCl_2$ for 16 hrs at 37° C. The gels were then stained using Blue Stain Reagent (Thermo Scientific). MMPs were visualized as light areas of digested gelatin against a darkly stained protein background. MMP2 is the major gelatinase secreted by HDFs as determined by MW. FIG. 3 shows that levels of MMP2 are reduced by 70% after treatment of HDFs with 25 mM MOHA.

EXAMPLE 4

Inhibition of Cancer Cell Proliferation

Figure 4:
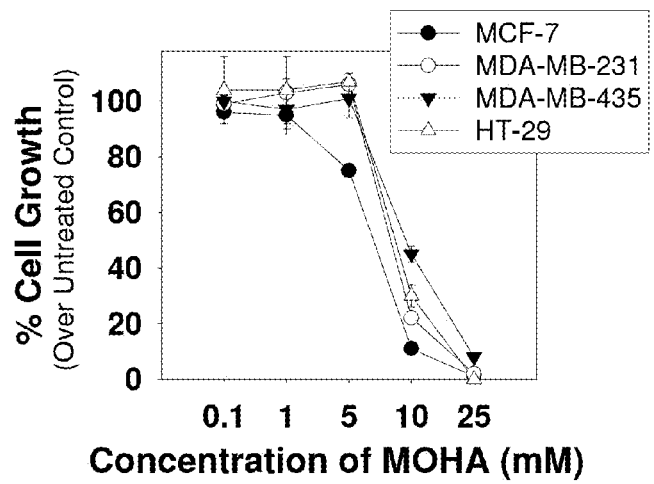
FIG. 4 shows inhibition of cell proliferation after treatment of MCF-7, MDA-MB-231, MDA-MB-435, and HT-29 cancer cells with MOHA.

MCF-7, MDA-MB-231, MDA-MB-435, or HT-29 cancer cells were plated onto a 96-well plate at a cell density of 2,000 cells per well. The cells were allowed to adhere overnight before they were treated with various concentrations of MOHA. They were then allowed to proliferate for 72 hrs. Cell numbers were determined at the end of the assay using a Cyquant proliferation kit (Invitrogen). FIG. 4 indicates that MOHA inhibits cell growth of tumor cells with an $IC_{50}$ value between 5 and 10 mM.

EXAMPLE 5

Figure 5:
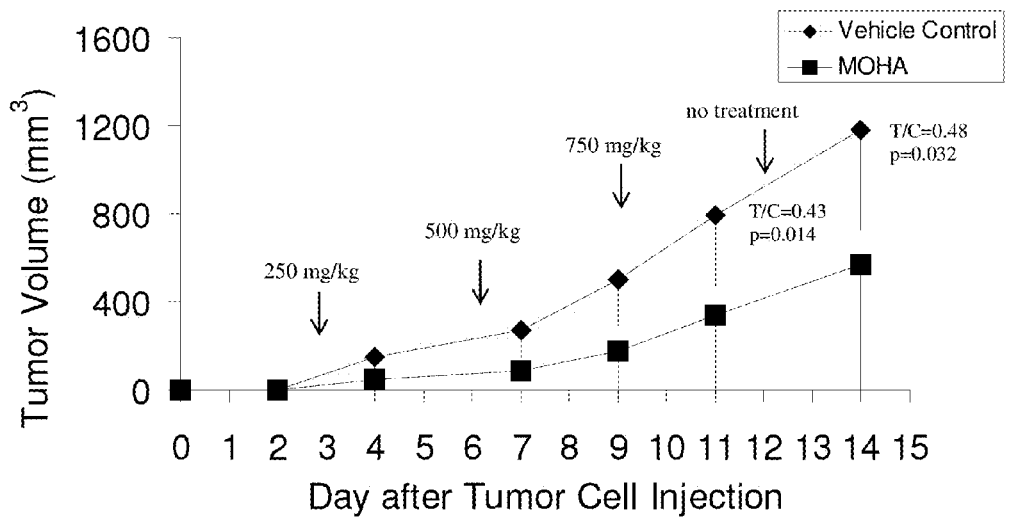
FIG. 5 shows inhibition of primary tumor growth in mice bearing 4T1 breast carcinomas following administration of escalating doses of MOHA.

Inhibition of Tumor Growth Following Treatment of Mice Bearing 4T1 Breast Carcinomas with MOHA Balb/c female mice were injected with $2\times10^5$ murine 4T1 breast cancer cells in the mammary fat pad. Treatment started 3 days after tumor cell inoculation and continued for 9 days. The study involved two group of animals (n=8/group). Control mice received vehicle (PBS), while treated mice received daily i.p. injections of MOHA at the indicated doses. Treatment was terminated 12 days after tumor cell inoculation and the study ended two days after the last treatment with MOHA. FIG. 5 shows that, at the end of the study, mice receiving MOHA experienced a ~50% reduction in their primary tumor growth.

EXAMPLE 6

Figures 6, 7:
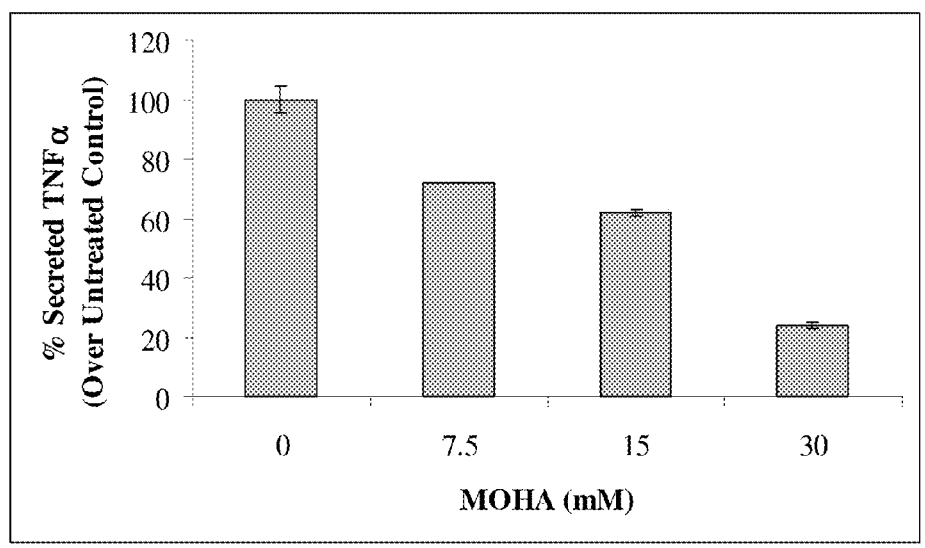
FIG. 6 shows inhibition of TNFα secretion from THP-1-derived macrophages following treatment with MOHA.
FIG. 7 shows reduction of collagen-induced arthritis in mice treated with MOHA.

Inhibition of TNFα Secretion Following Treatment of LPS-Stimulated Macrophages with MOHA Macrophages, derived from human monocytic THP-1 cells ($7.5\times10^4$ cells/well of a 96-well plate) after stimulation with 200 nM PMA for 96 hrs, were activated with 1 µg/mL LPS for 6 hrs in serum-free media in the absence and presence of various concentrations of MOHA. Conditioned media were then collected, normalized per cell number and analyzed for the presence of TNFα using an ELISA kit from Biolegend. FIG. 6 shows suppression of TNFα secretion following treatment of THP-1-derived macrophages with MOHA.

EXAMPLE 7

Inhibition of MMP9 Secretion after Treatment of Macrophages with MOHA in the Absence or Presence of CypA Activation Macrophages, derived from human monocytic THP-1 cells after stimulation with 200 nM PMA for 96 hrs, were treated with 10 mM MOHA in the absence or presence of 200 ng/mL cyclophilin A (CypA) for 24 hrs in serum-free media. Conditioned media corresponding to equal numbers of adherent cells were subjected to SDS-PAGE electrophoresis and Western immunoblotting against MMP9. Protein expression levels were estimated by Image J. FIG. 7 shows inhibition of MMP9 secretion from unstimulated and CypA-stimulated THP-1-derived macrophages after treatment with the cells with 10 mM MOHA.

EXAMPLE 8

Inhibition of Arthritis in Mice with Collagen Induced Arthritis (CIA) Following Treatment with MOHA DBA/1 mice, 6-8 weeks old, were injected s.c at the base of their tail with 100 mg of bovine type II collagen emulsified in complete Freund's adjuvant. At day 21 post-immunization, the mice were given a booster injection of 100 mg of bovine type II collagen emulsified in incomplete Freund's adjuvant. The experiment included two groups (n=10), which received 1000 mg/Kg MOHA or vehicle (Cremophor El) control orally, every day, excluding weekends, for four weeks. Treatment started when the clinical symptoms of arthritis became visible and disease was established. Development of arthritis was assessed every other day and scored on a scale of 0-4 as follows: 0=no edema or swelling, 1=slight edema and erythema restricted to the foot or ankle, 2=moderate to severe edema and erythema restricted to the foot or ankle, 3=edema and erythema of the entire paw, and 4=maximum inflamed limb involving multiple joints. The maximal arthritic score per animal was 16.

At the end of the study, termical sera were collected and analyzed for the presence of pro-inflammatory cytokines and proteins involved in bone erosion. Moreover, three front and four hind paws were selected from each groups for histological evaluation. The sections were evaluated blindly and scored for inflammation, pannus infiltration, cartilage damage, and bone erosion according to scale shown here.

Inflammation: 0=Normal, 1=Minimal infiltration of inflammatory cells in synovium and periarticular tissue of affected joints, 2=Mild infiltration, if paws, restricted to affected joints, 3=Moderate infiltration with moderate edema, if paws, restricted to affected joints, 4=Marked infiltration affecting most areas with marked edema, 5=Severe diffuse infiltration with severe edema.

Pannus: 0=Normal, 1=Minimal infiltration of pannus in cartilage and subchondral bone, 2=Mild infiltration with marginal zone destruction of hard tissue in affected joints, 3=Moderate infiltration with moderate hard tissue destruction in affected joints, 4=Marked infiltration with marked destruction of joint architecture, most joints, 5=Severe infiltration associated with total or near total destruction of, joint architecture, affects all joints.

Cartilage Damage: 0=Normal, 1=Minimal=minimal to mild loss of toluidine blue staining with no obvious chondrocyte loss or collagen disruption in affected joints, 2=Mild=mild loss of toluidine blue staining with focal mild (superficial) chondrocyte loss and/or collagen disruption in affected joints, 3=Moderate=moderate loss of toluidine blue staining with multifocal moderate (depth to middle zone) chondrocyte loss and/or collagen disruption inaffected joints, 4=Marked=marked loss of toluidine blue staining with multifocal marked (depth to deep zone) chondrocyte loss and/or collagen disruption in most joints, 5=Severe=severe diffuse loss of toluidine blue staining with multifocal severe (depth to tide mark) chondrocyte loss and/or collagen disruption in all joints. Bone Resorption: 0=Normal, 1=Minimal=small areas of resorption, not readily apparent on low magnification, rare osteoclasts in affected joints, 2=Mild=more numerous areas of, not readily apparent on low magnification, osteoclasts more numerous in affected joints, 3=Moderate=obvious resorption of medullary trabecular and cortical bone without full thickness defects in cortex, loss of some medullary trabeculae, lesion apparent on low magnification, osteoclasts more numerous in affected joints, 4=Marked=Full thickness defects in cortical bone, often with distortion of profile of remaining cortical surface, marked loss of medullary bone, numerous osteoclasts, affects most joints, 5=Severe=Full thickness defects in cortical bone and destruction of joint architecture of all joints.

Figure 8:
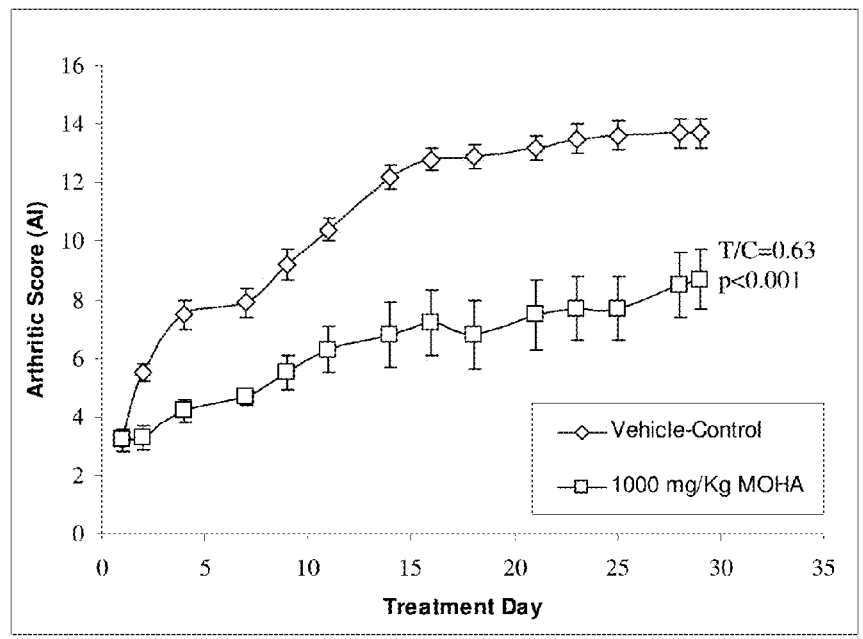
FIG. 8 shows reduction in the mean Arthritic Index (AI) in mice with collagen-induced arthritis (CIA) after treatment with MOHA.
Figure 9:
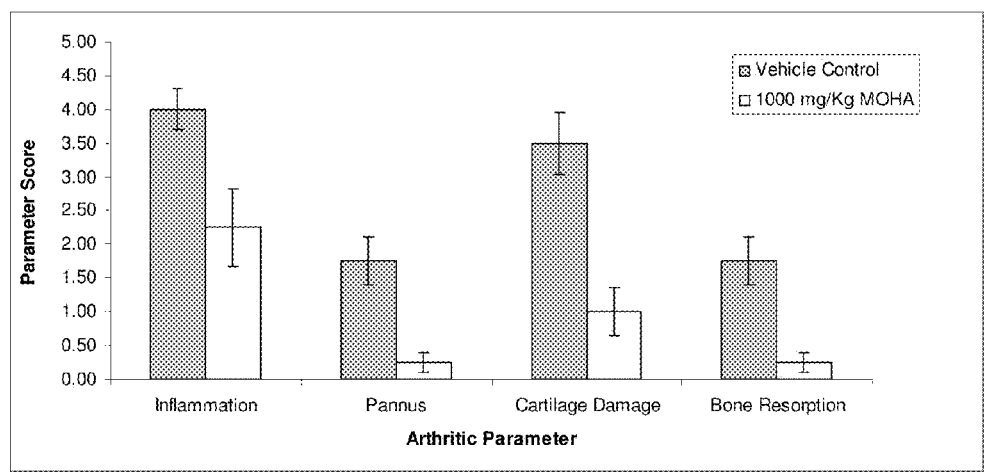
FIG. 9 shows reduction of various histological parameters associated with advanced arthritis in mice with CIA after treatment with MOHA.
Figure 10:
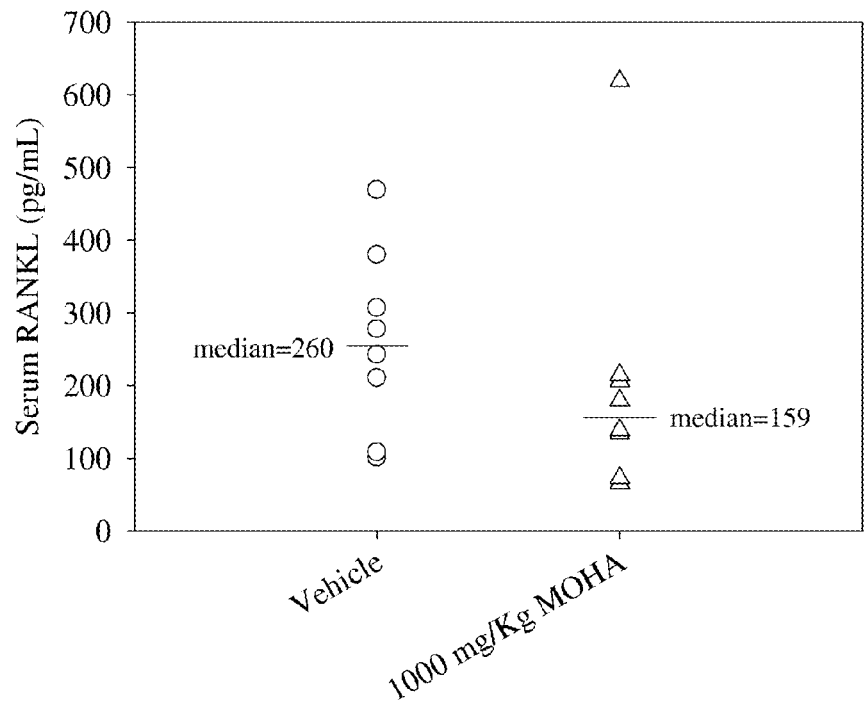
FIG. 10 shows reduction in the circulating levels of RANKL of mice with CIA following treatment with MOHA

FIG. 8 shows substantial inhibition of the symptomatic manifestation of arthritis in mice with collagen-induced arthritis CIA after treatment with MOHA. FIG. 9 shows substantial inhibition of all histological parameters examined following treatment of CIA-bearing mice with MOHA. The effect of MOHA on bone resorption is the most pronounced indicating that MOHA is particularly effective in reducing bone erosion. FIG. 10 shows a reduction in the levels of circulating RANKL following treatment of CIA-bearing mice with MOHA.

EXAMPLE 9

Figure 11:
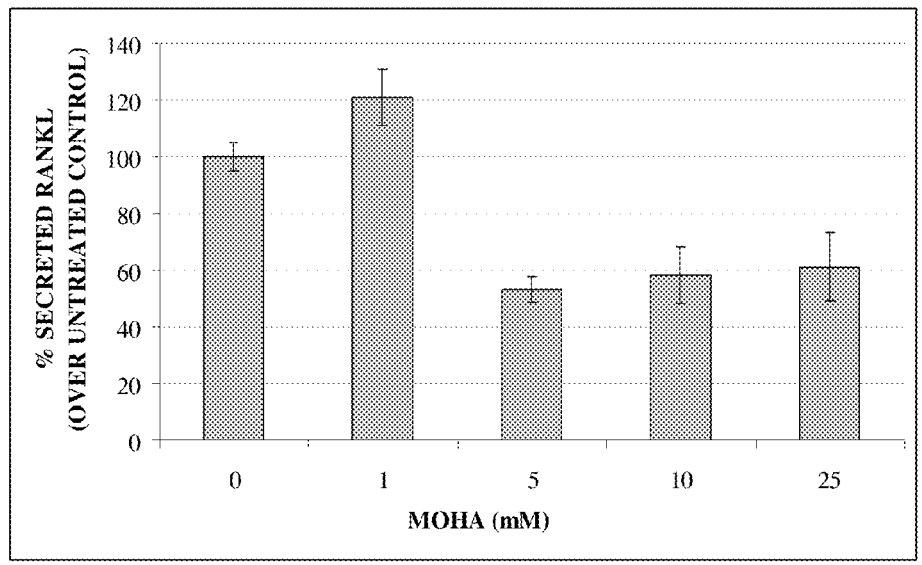
FIG. 11 shows reduction in the levels of secreted RANKL from pre-osteoblastic murine MC3T3 following treatment of the cells with MOHA.

Inhibition of RANKL Secretion Following Treatment of MC3T3 Pre-Osteoblastic Cells with MOHA MC3T3 pre-osteoblastic cells were plated onto a 96 well-plate at a cell density of $7.5 \times 10^4$ cells/well and allowed to adhere overnight. They were then stimulated with 1 µg/mL LPS and treated with various concentrations of MOHA for 24 hrs. Conditioned media were then collected, normalized per cell number and analyzed for the presence of RANKL using an ELISA kit from Abcam. FIG. 11 shows inhibition of RANKL secretion following treatment of LPS-stimulated MC3T3 cells with MOHA.

All documents, papers and published materials referenced herein, including books, journal articles, manuals, patent applications, published patent applications and patents, are expressly incorporated herein by reference in their entireties.

What is claimed is:

1. A method for treating an autoimmune inflammatory disease in a subject, comprising administering to a subject having an autoimmune inflammatory disease a therapeutically effective amount of a BCAT1 inhibitor and a pharmaceutically acceptable carrier, where the BCAT1 inhibitor is selected from the group of compounds encompassed by formula (1):

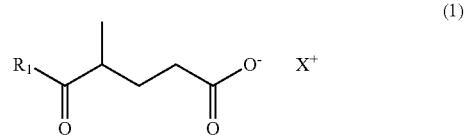

(1)

where $R_1$ is a linear alkyl group and $X^+$ denotes a cation, and where the autoimmune inflammatory disease is selected from the group consisting of systemic lupus erythematosus, rheumatoid arthritis (RA), multiple sclerosis (MS), psoriasis, and inflammatory bowel disease.

2. The method of claim 1, wherein the cation is selected from the group consisting of $H^+$, $Na^+$, $K^+$, and $NH_4^+$.

3. The method of claim 1, wherein the BCAT1 inhibitor is 4-methyl-5-oxohexanoic acid or a salt thereof.

4. The method of claim 1, wherein the subject is a human.

* * * * *